United States Patent
Li et al.

(10) Patent No.: US 8,530,405 B2
(45) Date of Patent: Sep. 10, 2013

(54) METHOD OF PREPARING WATER-SOLUBLE AND BIODEGRADABLE ANTIMICROBIAL AGENT

(75) Inventors: Chun-Yi Li, Zhongli (TW); Ken-Yuan Chang, Zhongli (TW); Chia-Chang Liu, Zhongli (TW); Ying-Nan Tsai, Zhongli (TW)

(73) Assignee: Far Eastern New Century Corporation, Taipei (TW)

( * ) Notice: Subject to any disclaimer, the term of this patent is extended or adjusted under 35 U.S.C. 154(b) by 69 days.

(21) Appl. No.: 13/098,814

(22) Filed: May 2, 2011

(65) Prior Publication Data

US 2012/0083439 A1 Apr. 5, 2012

(30) Foreign Application Priority Data

Oct. 4, 2010 (TW) ................................ 99133718 A

(51) Int. Cl.
- *A01N 37/18* (2006.01)
- *A61K 38/00* (2006.01)
- *A61P 31/00* (2006.01)

(52) U.S. Cl.
USPC ........................................... 514/1.1; 514/2.3

(58) Field of Classification Search
None
See application file for complete search history.

(56) References Cited

U.S. PATENT DOCUMENTS

| | | | |
|---|---|---|---|
| 5,126,057 A | | 6/1992 | Worley et al. |
| 5,292,864 A | * | 3/1994 | Wood et al. ............... 528/490 |
| 5,902,818 A | | 5/1999 | Worley et al. |
| 6,743,372 B1 | * | 6/2004 | Kleinstuck et al. ........... 252/181 |
| 7,335,373 B2 | | 2/2008 | Worley et al. |
| 2009/0042161 A1 | * | 2/2009 | Jodaikin et al. ................. 433/80 |
| 2009/0104251 A1 | * | 4/2009 | Lee ............................... 424/439 |

FOREIGN PATENT DOCUMENTS

| | | | |
|---|---|---|---|
| CN | 1312776 | * | 9/2001 |
| CN | 1312776 A | | 9/2001 |
| CN | 101633722 | * | 1/2010 |
| CN | 101633722 A | | 1/2010 |

OTHER PUBLICATIONS

Calbiochem Buffers Booklet, 2006.*
Parks et al, Neutrophil enhancement of *Pseudomonas aeruginosa* biofilm development: human F-actin and DNA as targets for therapy, Journal of Medical Microbiology (2009), 58, 492-502.*
English translation of abstract of CN 101633722 A (published Jan. 27, 2010).
English translation of abstract of CN 1312776 A (published Sep. 12, 2001).

* cited by examiner

*Primary Examiner* — Cecilia J Tsang
*Assistant Examiner* — Sergio Coffa
(74) *Attorney, Agent, or Firm* — McClure, Qualey & Rodack, LLP

(57) ABSTRACT

A method of preparing a water-soluble and biodegradable antimicrobial agent is provided. The method includes treating a polypeptide compound with sodium hypochlorite for at least 1 min, such that the polypeptide compound has at least one N-halamine group and has good antimicrobial effect. By using the method of the present invention, a chemical synthesis process is not required and an organic solvent is not required either, and thus, an antimicrobial agent having high water solubility, biodegradability, non-toxicity, good sterilization effect, and regeneration can be prepared with reduced harms to the environment.

15 Claims, 1 Drawing Sheet

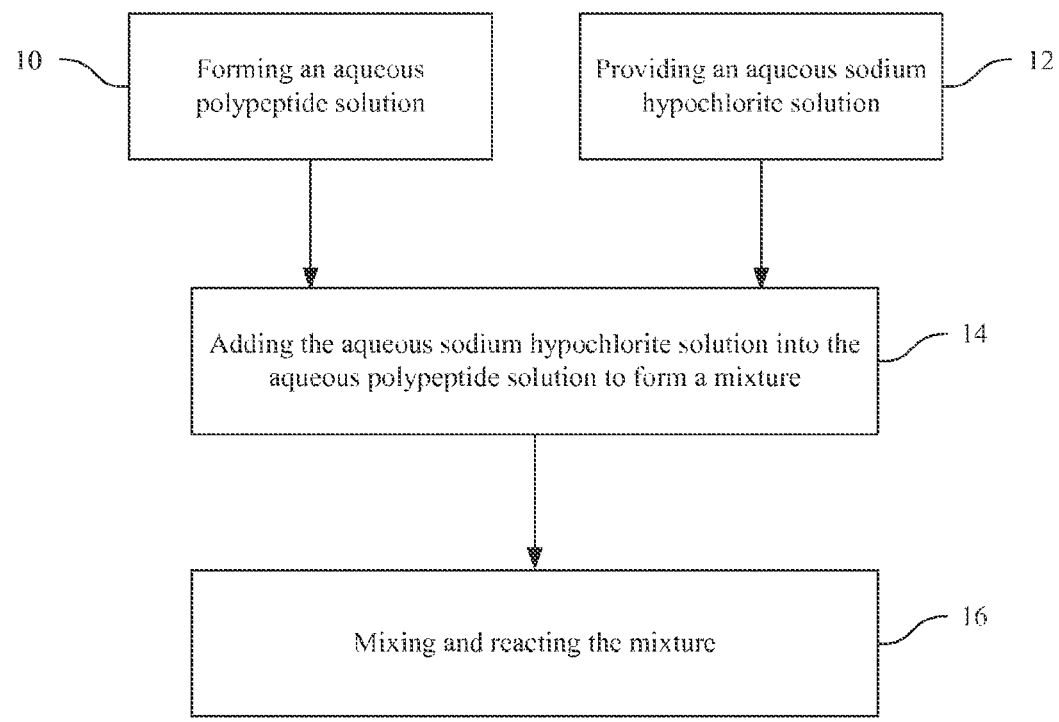

METHOD OF PREPARING WATER-SOLUBLE AND BIODEGRADABLE ANTIMICROBIAL AGENT

RELATED APPLICATIONS

This application claims priority to Taiwan Application Serial Number 099133718, filed Oct. 4, 2010, which is herein incorporated by reference.

BACKGROUND

1. Field of Invention

The present invention relates to a method of preparing a water-soluble and biodegradable antimicrobial agent, and more particularly, the present invention relates to a method of preparing a polypeptide chloride containing N-halamine groups.

2. Description of Related Art

In our living environments, even on the human body, the presence of at least thousands of microorganisms can be found. Among the microorganisms, some are beneficial to humans and some are harmful. Beneficial microorganisms can be used to produce desired foods or chemicals, and harmful microorganisms may destroy foods or drugs in processing, storage and transportation, or in use by consumers, or even cause an infection of tissues in body. Thus, in order to avoid the potential harms by such microorganisms to humans, there exists the need for antimicrobial agents in our living environments and various applications. It is currently known that many antimicrobial agents have been developed and widely used in various living applications.

Among currently developed antimicrobial agents of various types, there is a class of antimicrobial agent containing an N-halamine compound as a component, which has excellent antimicrobial efficacy for bacteria, molds and viruses and the like. It is known that an N-halamine compound refers to a compound containing a halamine functional group of N—X (X may be Cl, Br, or I), which can be obtained by oxidation of a compound containing a functional group, such as amine, amide, or imide group, with an oxidant (for example, hypohalites). The N—X functional group in this type of compounds can slowly dissociate by the action of water molecules in water in the presence of microorganisms, to release oxidizing halogen ions, while the N—X functional group in this compound is reduced to an N—H functional group. The released oxidizing halogen ions can kill microorganisms such as bacteria and molds. After the N-halamine compound dissociates into the halogen ion to kill the microorganisms, it usually can be treated with the hypohalites above again, so that the N—H functional group thereof can be oxidized into the N—X functional group again, thereby causing the regeneration of the sterilization function. It is known that the N-halamine compound is very useful for disinfection in family, commercial and medical places, due to having the advantages such as fast sterilization speed, high sterilization efficiency, long duration, good stability, and regeneratability of antimicrobial capability.

The research by Worley is the most representative of all the development of conventional antimicrobial N-halamine compounds. The research group leaded by Worley has developed many kinds of N-halamine compounds having antimicrobial property. However, all of these compounds are based on a cyclic N-halamine compound, and the structures disclosed are, for example, oxazolidinones (U.S. Pat. No. 5,902,818), imidazolidinones (U.S. Pat. No. 5,126,057), hydantoins, and spirocyclic amines, and the like. All of these structures are treated with hypochlorites to yield the N—Cl functional group, thereby having the antimicrobial efficacy; however, whether for these monomers or the polymer, the problem of less solubility in water exists, such that its application fields, even antimicrobial property, are limited.

On the other hand, based on the protection of environment, antimicrobial agent systems nowadays mostly tend to use an aqueous system instead of an organic solvent, thereby reducing the harms by the organic solvent to the environment.

In order to be applicable in the aqueous system, Worley et al considered that a hydrophilic group can be attached onto a side chain of the polymer to obtain an antimicrobial substance having high water solubility. A quaternary ammonium salt is generally used as the hydrophilic group, thereby improving the solubility in water. For example, Worley et al has developed an antimicrobial polymer in which siloxane is used as the skeleton and a cyclic N-halamine compound hydantoin and quaternary ammonium salt structures are attached thereon, respectively (U.S. Pat. No. 7,335,373). Therein, both siloxane and hydantoin have very poor solubility in water, and the water solubility of the antimicrobial polymer is improved mainly by the quaternary ammonium salt, which has no antimicrobial efficacy, and therefore, a longer contact time is required for such an antimicrobial agent to achieve the sufficient antimicrobial effect. Although Worley et al has designed this antimicrobial polymer structure by improving the water solubility of the cyclic N-halamine compound, the problem that it is not totally soluble in water still exists and a small amount of alcohols still needs to be added to help to dissolve the antimicrobial polymer for using the cyclic N-halamine compound. However, this cannot completely resolve the doubts about the likely harms caused by the organic solvent to the environment. On the other hand, the structure of this antimicrobial polymer is obtained by the chemical synthesis, and during and after the synthesis, organic solvents may be used more or less and unnecessary side-products may be generated, thus, the harms caused to the environment may also occur in the manufacturing process to some extent. Furthermore, a special synthesis via multiple preparation processes is needed for such an antimicrobial polymer, which would thus be expensive. This can be confirmed by the fact that techniques for preparing such compound had been disclosed by Worley et al many years before, but up to now, no numerous products have been marketed.

Therefore, it is necessary to develop a water-soluble and antimicrobial substance having biocompatibility, non-toxicity, regenerative antimicrobial capability, easy preparation, and low cost.

SUMMARY

A primary aspect of the present invention is to provide a method of preparing an antimicrobial agent having high water solubility and biodegradability.

A method of preparing an aqueous biodegradable antimicrobial solution according to the present invention comprises the following steps: (a) forming an aqueous polypeptide solution by providing a polypeptide compound and dissolving it into an aqueous solution; (b) providing an aqueous sodium hypochlorite solution; (c) adding the aqueous sodium hypochlorite solution into the aqueous polypeptide solution to form a mixture; and (d) mixing the mixture for at least 1 min at room temperature, such that the polypeptide compound is reacted with sodium hypochlorite in the aqueous sodium hypochlorite solution, thereby forming a polypeptide chloride.

The polypeptide chloride described in the step above has at least one N-halamine groups of N—Cl. Particularly, the polypeptide compound is a polyglutamic acid or polyaspartic acid, and the polypeptide chloride is a polyglutamic acid chloride or polyaspartic acid chloride.

The preparation method of the present invention does not cause the harm to the environment, because the process is non-toxic and the use of an organic solvent is not required. In addition, the preparation method of the present invention has the advantages such as simple process (due to no need for a complex and time-consuming chemical synthesis process), high yield, and low cost and the like.

In addition, by using the preparation method of the present invention, an antimicrobial agent that has the advantages such as high sterilization efficiency, long duration, and regeneration of antimicrobial property can be easily prepared.

Thus, by using the preparation method of the present invention, the problems that when an antimicrobial agent comprising a cyclic N-halamine compound as a component is conventionally synthesized, a large amount of an organic solvent is required, an aqueous phase solution cannot be used as solvent alone for the compound and the compound has no biodegradablity such that the harm to the environment is easily caused can be well solved.

It is to be understood that both the foregoing general description and the following detailed description are by examples, and are intended to provide further explanation of the invention as claimed.

BRIEF DESCRIPTION OF THE DRAWINGS

The invention can be more fully understood by reading the following detailed description of the embodiment, with reference made to the accompanying drawings as follows:

FIG. 1 is a process flow diagram of the present invention.

DETAILED DESCRIPTION

In order to achieve the aspects above, the preparation method as disclosed in the present invention comprises the following steps:

An aqueous polypeptide solution is formed by dissolving a polypeptide into an aqueous solution. Additionally, an aqueous sodium hypochlorite solution is provided, and then the aqueous sodium hypochlorite solution is added into the aqueous polypeptide solution to form a mixture. Then, the mixture is mixed for at least 1 min at room temperature, such that the polypeptide compound is reacted with sodium hypochlorite in the aqueous sodium hypochlorite solution, thereby forming a polypeptide chloride. Therein, the polypeptide chloride has at least one N-halamine groups of N—Cl.

To enable those skilled in the art to understand the invention, reference will now be made to FIG. 1, in which the method of preparing a water-soluble and biodegradable antimicrobial agent according to the present invention is disclosed.

At first, in step 10 of FIG. 1, an aqueous polypeptide solution is formed by providing a polypeptide compound and dissolving it into an aqueous solution. In addition, an aqueous sodium hypochlorite solution is provided in step 12.

It is known that the polypeptide compound is a polymer formed of a plurality of amino acid units linked by peptide bonds. The source of the polypeptide compound useful in the present invention is not particularly limited, and it can be obtained from a naturally-occurring substance by microbial fermentation, or can also be isolated from a naturally-occurring substance, and thus it is essentially a natural non-toxic substance. Moreover, with the development of modern techniques, if required, a desired peptide sequence can also be synthesized by using a known peptide synthesizer.

In addition, final degradation products of the polypeptide compound are $NH_3$, $CO_2$, and $H_2O$, which are harmless to the environment, thus, it is a biodegradable and environment-friendly compound, and accordingly, use of the compound as a raw material does not have the defects of known chemically synthetic antimicrobial compounds. However, because the peptide bonds in the backbone structure of the polypeptide compound can easily be broken by action of, for example, microorganisms and fungi, and the broken oligopeptides or amino acid monomers remain a nutrient source for microorganisms, known polypeptide compounds not only do not have the antimicrobial property, but also easily nourish the growth of bacteria. Nonetheless, after being modified by the preparation method of this invention, the known polypeptide compounds can be provided with the antimicrobial property.

The class of the polypeptide compound useful in the present invention is essentially not particularly limited; however, in consideration of ease of availability, preferred are polyglutamic acid and polyaspartic acid, having the following formulas (I) and (II), respectively:

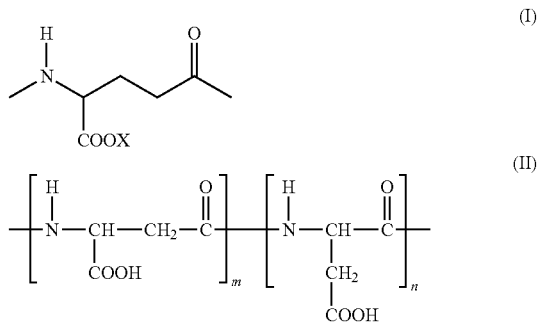

in which, $m \geq n$.

The preparation method of the aqueous polypeptide solution useful in the present invention is not particularly limited, as long as it is any method known to prepare the aqueous polypeptide solution. For example, the polypeptide compound is added into purified water and stirred until it is completely dissolved, thereby achieving a desired operation concentration.

The operation concentration of the aqueous polypeptide solution and the concentration of the aqueous sodium hypochlorite solution are not particularly limited, as long as the polypeptide chloride formed after the aqueous polypeptide solution is reacted with the aqueous sodium hypochlorite solution reaches a minimum content of the N-halamine groups. Then, the aqueous sodium hypochlorite solution is added into the aqueous polypeptide solution to form a mixture in step 14. For ease of operation, in the mixture above, the added amount of sodium hypochlorite in the aqueous sodium hypochlorite solution is preferably to be 5-100 weight parts, and more preferably 35-50 weight parts, based on 100 weight parts of the total amount of the polypeptide compound in the aqueous polypeptide solution.

Finally, the mixture is mixed and reacted in step 16, such that the polypeptide compound is reacted with sodium hypochlorite in the aqueous sodium hypochlorite solution, thereby forming a polypeptide chloride having at least one N-halamine groups of N—Cl.

The content of the N-halamine groups, as described above, refers to a weight percentage of all N-halamine groups relative to the total weight of the polypeptide chloride. The minimum content of the N-halamine groups, as described herein, preferably is not less than 0.3 wt %, and more preferably is in the range of 0.3-15 wt %, at which the antimicrobial efficacy can be achieved. In addition, when the polypeptide chloride of this invention is dissolved in water to prepare an antimicrobial agent, where the content of the N-halamine groups of the polypeptide chloride in the antimicrobial agent is not less than 100 ppm to achieve the antimicrobial efficacy; further preferred is 200-10000 ppm.

The mixing time above is preferably at least 1 min, more preferably at least 30 min, and most preferably 90-180 min, such that there is a sufficient mixing time for the polypeptide compound in the mixture and sodium hypochlorite in the aqueous sodium hypochlorite solution to form the polypeptide chloride having the antimicrobial effect.

According to the preparation method of this invention, the N—H functional groups in the polypeptide compound are oxidized into the N-halamine groups by reacting the polypeptide compound with sodium hypochlorite in the aqueous sodium hypochlorite solution. It can be easily concluded from the disclosure of this invention by those skilled in the art that, Cl in the N-halamine group can also be replaced by Br or I. Therefore, other classes of halogenating agents having an equivalent oxidation efficacy can be used in place of sodium hypochlorite in the aqueous sodium hypochlorite solution to react with the polypeptide compound.

For the antimicrobial agent prepared by the preparation method of this invention, the polypeptide chloride in the antimicrobial agent can slowly dissociate by the action of water molecules in water in the presence of microorganisms, to release oxidizing halogen ions, which can kill microorganisms such as bacteria and molds, and thus the antimicrobial efficacy can be obtained.

In addition, in the preparation method of this invention, the aqueous sodium hypochlorite solution is an oxidant, thus, the temperature of the mixture above preferably is kept at room temperature, so as to avoid the possibility of $Cl_2$ release due to a violent reaction at an elevated temperature.

In the step 16 of reacting the mixture above, in order to react the polypeptide compound with sodium hypochlorite in the aqueous sodium hypochlorite solution more rapidly, an external force can be applied to the mixture to agitate it. For example, any other applicable means well-known by those skilled in the art, such as magnetic stirring, homogenization, paddle stirring, can be used, and the present invention is not limited thereto.

For a better effect of the preparation method of this invention, the mixture above has preferably a pH in the range of 6-8; under a basic environment of a too high pH, the reaction rate of the polypeptide compound and sodium hypochlorite in the aqueous sodium hypochlorite solution is easily reduced, the oxidation degree is low and the effect is poor, and where the pH is less than 6, the reaction rate is easily increased, resulting in the breakage of amide bonds and the decrease of molecular weight, such that the structure of the polypeptide compound is destroyed.

In order to control and maintain the pH of the mixture solution above within the preferred range above during the reaction, a pH buffer agent can be selectively added to the mixture solution to adjust the pH thereof.

The pH buffer agent useful in the present invention is not particularly limited, including, but not limited to, aqueous phosphoric acid solution, aqueous ammonium chloride solution, aqueous acetic acid solution, aqueous sodium hydrogen phosphate solution, aqueous disodium hydrogen phosphate solution, aqueous benzoic acid solution, or a mixture thereof.

The content of the polypeptide chloride in the antimicrobial agent prepared by the preparation method of this invention is preferably not higher than 10 wt %, so as to avoid the case where the content of the antimicrobial polymer in the solution is too high, such that the polymer is reacted with water to release an irritating halogen gas.

From the disclosure of this invention, those skilled in the art will appreciate that the polypeptide chloride prepared by the preparation method of this invention can also be prepared in a solid form. For example, a solid powder of the polypeptide chloride can be obtained by precipitate the polypeptide chloride and then drying it, using the known solvent-non-solvent method. The solvent-non-solvent method is to utilize the very low solubility or insolubility of the polypeptide chloride for a non-solvent, in which the non-solvent is added to induce the precipitation of the polypeptide chloride from water, forming a phase separation state. The non-solvent useful in the solvent-non-solvent method of this invention must be miscible with water, and the polypeptide chloride has a very low solubility therein to precipitate out. For example, the non-solvent can include, but is not limited to, isopropanol, methanol, ethanol, acetone, or acetonitrile.

Several examples are set forth below to describe the method of the present invention in more detail, which, however, are for illustrative purposes only and are not intended to limit the present invention, and the scope of the present invention is defined by the appended claims.

EXAMPLES

Determination of Content of N-Halamine Group

The determination of the content of the N-halamine group in the polyglutamic acid chloride was carried out by a titration method, comprising:

1. At first, 5 g sodium thiosulfate (Aldrich, US) was diluted with purified water to 200 ml, to prepare a sodium thiosulfate titrant.

2. 0.5 g of the polyglutamic acid chloride after oxidation reaction was weighted, and then 1 g KI powder (Aldrich, US) and 40 ml purified water were added and continuously stirred until the powder was totally dissolved. If necessary, a small amount of acetic acid could be added as catalyst.

3. The mixture in step 2 was titrated with the sodium thiosulfate titrant in step 1, using a starch reagent (Aldrich, US) as indicator. A titration end point is reached as the solution turns colorless and clear from reddish-brown. The volume of the sodium thiosulfate titrant used was recorded.

4. The reaction equation of the titration is shown in the formula (a) below:

$$NCl + 2I^- + H^+ \rightarrow Cl^- + NH + I_2$$

$$I_2 + 2S_2O_3^{2-} \rightarrow 2I^- + S_4O_6^{2-} \qquad (a)$$

According to this reaction equation, the content of the N-halamine group per g polyglutamic acid chloride could be obtained by the moles of the sodium thiosulfate titrant used. The determination of the content of the N-halamine group in the polyaspartic acid chloride could be carried out according to the titration method above, provided that the polyglutamic acid chloride was substituted with the polyaspartic acid chloride.

Preparation of Polyglutamic Acid Chlorides Having Various Contents of N-Halamine Group

Example 1

10.0 g polyglutamic acid (PGA-Na$^+$, Mw~2,000,000, Vedan, Taiwan) was placed into a 250 ml one-necked flask, and 90 ml purified water was added to dissolve it, to prepare an aqueous polyglutamic acid solution. Then, 4 g of 12.65 wt % aqueous sodium hypochlorite solution was added to form a mixture. The mixture was continuously stirred for 30 min at room temperature, so that polyglutamic acid was reacted with sodium hypochlorite. The reacted mixture was placed in a separatory funnel to precipitate the polyglutamic acid chloride with isopropanol, which was separated from the funnel and dried in a vacuum oven. The dried product was a white to yellowish powder, which was totally soluble when it was dissolved in water. The dried polyglutamic acid chloride was titrated with sodium thiosulfate, and finally, the content of the N-halamine group per g polyglutamic acid chloride was calculated.

Examples 2-6

The same procedures as described in example 1 were used, except that the aqueous sodium hypochlorite solution was added to the aqueous polyglutamic acid solution at a weight of 12, 20, 28, 36, and 40 g, respectively. The mixtures were continuously stirred for 30 min at room temperature, so that polyglutamic acid was reacted with sodium hypochlorite. The reacted mixtures were placed in a separatory funnel to precipitate the polyglutamic acid chlorides with isopropanol, which were separated from the funnel and dried in a vacuum oven. The dried products each were a white to yellowish powder, which were totally soluble when they were dissolved in water. The dried polyglutamic acid chlorides were titrated with sodium thiosulfate, and finally, the contents of the N-halamine group per g polyglutamic acid chloride was calculated.

Examples 7-8

The same procedures and mixture ratio as described in example 1 were used, except that the stirring time of the mixtures at room temperature was prolonged to 90 and 180 min respectively. After the reaction time was reached, similarly, the reacted mixtures were placed in a separatory funnel respectively to precipitate the polyglutamic acid chlorides with isopropanol, which were separated from the funnel and dried in a vacuum oven. The dried products each were a white to yellowish powder, which were totally soluble when they were dissolved in water. The dried polyglutamic acid chlorides were titrated with sodium thiosulfate, and finally, the contents of the N-halamine group per g polyglutamic acid chloride were calculated.

Example 9

The same procedures as described in example 1 were used, except that the aqueous sodium hypochlorite solution was added to the aqueous polyglutamic acid solution at a weight of 80 g. Moreover, the stirring time of the mixture at room temperature was prolonged to 1440 min. After the reaction time was reached, the reacted mixture was placed in a separatory funnel to precipitate the polyglutamic acid chloride with isopropanol, which was separated from the funnel and dried in a vacuum oven. The dried product was a white to yellowish powder, which was totally soluble when it was dissolved in water. The dried polyglutamic acid chloride was titrated with sodium thiosulfate, and finally, the content of the N-halamine group per g polyglutamic acid chloride was calculated.

Example 10

5.0 g polyglutamic acid was placed into a 500 ml one-necked flask, and 167 ml purified water was added to dissolve it, to prepare an aqueous polyglutamic acid solution. Then, 54 g of 4.89 wt % aqueous sodium hypochlorite solution was added, and the pH was adjusted to 6-8 with 0.5 N aqueous phosphoric acid solution, to form a mixture. The mixture was continuously stirred for 1 min at room temperature, so that polyglutamic acid was reacted with sodium hypochlorite. The reacted mixture was placed in a separatory funnel to precipitate the polyglutamic acid chloride with isopropanol, which was separated from the funnel and dried in a vacuum oven. The dried product was a white to yellowish powder, which was totally soluble when it was dissolved in water. The dried polyglutamic acid chloride was titrated with sodium thiosulfate, and finally, the content of the N-halamine group per g polyglutamic acid chloride was calculated.

Examples 11-12

The same procedures and mixture ratio as described in example 10 were used, except that the stirring time of the mixtures at room temperature was prolonged to 5 and 10 min respectively. After the reaction time was reached, similarly, the reacted mixtures were placed in a separatory funnel respectively to precipitate the polyglutamic acid chlorides with isopropanol, which were separated from the funnel and dried in a vacuum oven. The dried products each were a white to yellowish powder, which were totally soluble when they were dissolved in water. The dried polyglutamic acid chlorides were titrated with sodium thiosulfate, and finally, the contents of the N-halamine group per g polyglutamic acid chloride were calculated.

Preparation of Polyaspartic Acid Chlorides Having Various Contents of N-halamine Group

Example 13

10.0 g polyaspartic acid (PASP, MW~5000, Taihe Water Treatment, China) was placed into a 500 ml one-necked flask, and 80 ml purified water was added to dissolve it, to prepare an aqueous polyaspartic acid solution. Then, 94 g of 6.84 wt % aqueous sodium hypochlorite solution was added to form a mixture. The mixture was continuously stirred for 12 h at room temperature, so that polyaspartic acid was reacted with sodium hypochlorite. The reacted mixture was placed in a separatory funnel to precipitate the polyaspartic acid chloride with ethanol, which was separated from the funnel and dried in a vacuum oven. The dried product was a white to yellowish powder, which was totally soluble when it was dissolved in water. The dried polyaspartic acid chloride was titrated with sodium thiosulfate, and finally, the content of the N-halamine group per g polyaspartic acid chloride was calculated.

Example 14

10.0 g polyaspartic acid was placed into a 500 ml one-necked flask, and 80 ml purified water was added to dissolve it, to prepare an aqueous polyaspartic acid solution. Then, 188 g of 6.84 wt % aqueous sodium hypochlorite solution was added to form a mixture. The mixture was continuously stirred for 12 h at room temperature, so that polyaspartic acid was reacted with sodium hypochlorite. The reacted mixture was placed in a separatory funnel to precipitate the polyaspartic acid chloride with ethanol, which was separated from the funnel and dried in a vacuum oven. The dried product was a white to yellowish powder, which was totally soluble when it was dissolved in water. The dried polyaspartic acid chloride was titrated with sodium thiosulfate, and finally, the content of the N-halamine group per g polyaspartic acid chloride was calculated.

Example 15

10.0 g polyaspartic acid was placed into a 500 ml one-necked flask, and 50 ml purified water was added to dissolve it, to prepare an aqueous polyaspartic acid solution. Then, 70.2 g of 9.23 wt % aqueous sodium hypochlorite solution was added to form a mixture. The mixture was continuously stirred for 3 h at room temperature, so that polyaspartic acid was reacted with sodium hypochlorite. The reacted mixture was placed in a separatory funnel to precipitate the polyaspartic acid chloride with ethanol, which was separated from the funnel and dried in a vacuum oven. The dried product was a white to yellowish powder, which was totally soluble when it was dissolved in water. The dried polyaspartic acid chloride was titrated with sodium thiosulfate, and finally, the content of the N-halamine group per g polyaspartic acid chloride was calculated.

The mixture ratios, reaction time, and the content of the N-halamine group in the examples are summarized in tables 1 and 2 below.

TABLE 1

| Examples | PGA (g) | Aqueous Sodium Hypochlorite Solution (g) | Sodium Hypochlorite (g) | Reaction Time (min) | Content of N-halamine Group per g PGA Chloride (wt %) |
|---|---|---|---|---|---|
| 1 | 10 | 4 | 0.51 | 30 | 2.32 |
| 2 | 10 | 12 | 1.52 | 30 | 3.80 |
| 3 | 10 | 20 | 2.53 | 30 | 5.78 |
| 4 | 10 | 28 | 3.54 | 30 | 8.28 |
| 5 | 10 | 36 | 4.55 | 30 | 10.93 |
| 6 | 10 | 40 | 5.06 | 30 | 11.30 |
| 7 | 10 | 40 | 5.06 | 90 | 14.61 |
| 8 | 10 | 40 | 5.06 | 180 | 13.41 |
| 9 | 10 | 80 | 10.12 | 1440 | 7.74 |
| 10 | 5 | 54 | 2.64 | 1 | 0.66 |
| 11 | 5 | 54 | 2.64 | 5 | 1.00 |
| 12 | 5 | 54 | 2.64 | 10 | 2.08 |

TABLE 2

| Examples | PASP (g) | Aqueous Sodium Hypochlorite Solution (g) | Sodium Hypochlorite (g) | Reaction Time (hour) | Content N-halamine Group per g PASP Chloride (wt %) |
|---|---|---|---|---|---|
| 13 | 10 | 94 | 6.43 | 12 | 1.22 |
| 14 | 10 | 188 | 12.86 | 12 | 0.89 |
| 15 | 10 | 70.2 | 6.48 | 3 | 0.30 |

Antimicrobial Test

The antimicrobial activity test of most of antimicrobial agents was evaluated for resistance to a wide range of microorganisms including Gram-positive and Gram-negative microorganisms. The test bacteria of the present invention were *Staphylococcus aureus* (BCRC Number 15211) and *Escherichia coli* (BCRC Number 11446). Here, the *Staphylococcus aureus* is a Gram-positive bacterium and the *Escherichia coli* is a Gram-negative bacterium.

A. Culture of Strains

A single colony of the *Staphylococcus aureus* and a single colony of the *Escherichia coli* were picked from a preserved agar medium, and inoculated to a 15 mL centrifugal tube containing 2000 μL LB broth respectively. Then, the centrifugal tube was shaken for 10 min and after the bacteria was well dispersed and suspended, the formed stock solution was subjected to 10-fold serial dilution with LB broth, to obtain diluted solutions having various dilution factors ($10^{-1}$, $10^{-2}$, $10^{-3}$, $10^{-4}$, and $10^{-5}$). Afterwards, 100 μL the solutions of *Staphylococcus aureus* and *Escherichia coli* having various dilution factors were inoculated onto different agar media and uniformly plated with a triangular glass rod, respectively. Then, the agar media plated with the solutions were placed into an incubator at 37° C. and grown for 14-24 h, and at this time, the growth in the solutions having various dilution factors after plating could be observed and the colony forming units in the agar range (20-300 CFU) could be counted, whereby it can be confirmed that the bacteria can normally grow in this environment. Then, based on the calculated colony forming units in the agar media, a suitable amount of the stock solution was adjusted with sterile water, to obtain a test solution of $10^6$-$10^7$ CFU/mL.

B. Qualitative Antimicrobial Test

The two test solutions above (*Staphylococcus aureus* and *Escherichia coli*) of each 100 μL were inoculated onto different agar media and uniformly plated with a triangular glass rod, respectively. Next, the polypeptide chlorides prepared in the examples 1-15 (polyglutamic acid chlorides and polyaspartic acid chlorides) and untreated polypeptide chlorides were made into a tablet, respectively, and the tablets were horizontally adhered onto the agar media plated with the test solutions as described above, respectively. Then, the agar media were placed in an incubator at 37° C. and grown for 14-24 h, and at this time, the surface and surroundings of the tablets were observed. It could be clearly seen with the naked eye that, no colony was formed on the surface and surroundings of the tablets of the polypeptide chlorides, and there were colonies formed on those of the polypeptides.

C. Quantitative Antimicrobial Test

The evaluation in this test was carried out according to the antimicrobial standards of ASTM E2149 under dynamic contact conditions. In this test, the two test solutions above (*Staphylococcus aureus* and *Escherichia coli*) were diluted 10-fold to control the concentration to be $10^5$-$10^6$ CFU/mL, respectively, as test solutions of this test.

The polypeptide chlorides prepared in the examples 1-12 of each 125 mg and the polypeptide as control of 125 mg were weighted and inoculated with 5 mL of the test solutions and incubated. After 24 h of incubation, bacterial counts without incubation (A) and bacterial counts with incubation (B) after the polypeptide chlorides and control were inoculated with the bacterial solutions were determined respectively. After the resultant bacterial counts above were calculated, the antibacterial activity could be calculated by the following equation (b):

$$\text{Antibacterial activity} = \frac{A - B}{A} \times 100\% \quad \text{(b)}$$

in which, A is bacterial counts with inoculation and without incubation; B is bacterial counts with inoculation and with 24 h of incubation. When B is much greater than A, it is indicative of no antimicrobial activity. The antimicrobial activities of the examples 1-15 and control are shown in tables 3 and 4 below.

TABLE 3

Antimicrobial activity with *Staphylococcus aureus* as test solution (based on ASTM E2149 under dynamic contact conditions)

| | Colony Density (CFU/cm$^2$) | | Antimicrobial |
|---|---|---|---|
| | 0 h | 24 h | Activity (%) |
| Control | $3.65 \times 10^5$ | $7.97 \times 10^7$ | 0 |
| Example 1 | $3.51 \times 10^5$ | 0 | >99.9 |
| Example 2 | $2.98 \times 10^5$ | 0 | >99.9 |
| Example 3 | $3.44 \times 10^5$ | 0 | >99.9 |
| Example 4 | $2.89 \times 10^5$ | 0 | >99.9 |
| Example 5 | $3.82 \times 10^5$ | 0 | >99.9 |
| Example 6 | $3.36 \times 10^5$ | 0 | >99.9 |
| Example 7 | $3.51 \times 10^5$ | 0 | >99.9 |
| Example 8 | $3.73 \times 10^5$ | 0 | >99.9 |
| Example 9 | $3.27 \times 10^5$ | 0 | >99.9 |
| Example 10 | $2.95 \times 10^5$ | 0 | >99.9 |
| Example 11 | $2.99 \times 10^5$ | 0 | >99.9 |
| Example 12 | $3.01 \times 10^5$ | 0 | >99.9 |
| Example 13 | $3.22 \times 10^5$ | 0 | >99.9 |
| Example 14 | $3.53 \times 10^5$ | 0 | >99.9 |
| Example 15 | $3.48 \times 10^5$ | 0 | >99.9 |

TABLE 4

Antimicrobial activity with *Escherichia coli* as test solution (based on ASTM E2149 under dynamic contact conditions)

| | Colony Density (CFU/cm$^2$) | | Antimicrobial |
|---|---|---|---|
| | 0 h | 24 h | Activity (%) |
| Control | $2.82 \times 10^5$ | $6.50 \times 10^7$ | 0 |
| Example 1 | $3.13 \times 10^5$ | 0 | >99.9 |
| Example 2 | $3.44 \times 10^5$ | 0 | >99.9 |
| Example 3 | $3.57 \times 10^5$ | 0 | >99.9 |
| Example 4 | $3.46 \times 10^5$ | 0 | >99.9 |
| Example 5 | $3.22 \times 10^5$ | 0 | >99.9 |
| Example 6 | $3.61 \times 10^5$ | 0 | >99.9 |
| Example 7 | $3.37 \times 10^5$ | 0 | >99.9 |
| Example 8 | $3.76 \times 10^5$ | 0 | >99.9 |
| Example 9 | $3.56 \times 10^5$ | 0 | >99.9 |
| Example 10 | $3.45 \times 10^5$ | 0 | >99.9 |
| Example 11 | $3.34 \times 10^5$ | 0 | >99.9 |
| Example 12 | $3.59 \times 10^5$ | 0 | >99.9 |
| Example 13 | $3.15 \times 10^5$ | 0 | >99.9 |
| Example 14 | $3.26 \times 10^5$ | 0 | >99.9 |
| Example 15 | $3.37 \times 10^5$ | 0 | >99.9 |

D. Quantitative Antimicrobial Test

The evaluation in this test was carried out according to the antimicrobial standard of AATCC 100 under static contact conditions. The polypeptide chlorides prepared in the examples 1-12 and control were processed onto a cotton cloth by an impregnation and padding method, respectively, and they were cut into square specimens of 2×2 cm$^2$ in size, horizontally adhered onto the bottom of a 50 mL serum bottle, respectively and inoculated with 20 μL 10$^6$-10$^7$ CFU/mL of the test solutions (*Staphylococcus aureus* and *Escherichia coli*). After the test solutions were contacted with these square specimens, the square specimens were immediately washed with 20 mL sterile water, and bacteria counts with inoculation and without incubation (A) were determined. Another set of square specimens inoculated with the test solutions were taken, and these square specimens were incubated for 24 h after they were contacted with the test solutions, and then bacteria counts with incubation (B) were determined.

The antibacterial activities of the polypeptide chlorides and control could be calculated according to the equation (b) above. The antimicrobial activities of the examples 1-15 and control are shown in tables 5 and 6 below. In tables 5 and 6, the colony density (CFU/cm$^2$) refers to a value obtained by dividing the number of colonies counted in the range of 2×2 cm$^2$ by the area of this range.

TABLE 5

Antimicrobial activity with *Staphylococcus aureus* as test solution (based on AATCC 100 under static contact conditions)

| | Colony Density (CFU/cm$^2$) | | Antimicrobial |
|---|---|---|---|
| | 0 h | 24 h | Activity (%) |
| Control | $6.95 \times 10^5$ | $8.55 \times 10^7$ | 0 |
| Example 1 | $7.03 \times 10^5$ | 0 | >99.9 |
| Example 2 | $6.14 \times 10^5$ | 0 | >99.9 |
| Example 3 | $6.63 \times 10^5$ | 0 | >99.9 |
| Example 4 | $7.16 \times 10^5$ | 0 | >99.9 |
| Example 5 | $5.22 \times 10^5$ | 0 | >99.9 |
| Example 6 | $5.61 \times 10^5$ | 0 | >99.9 |
| Example 7 | $6.37 \times 10^5$ | 0 | >99.9 |
| Example 8 | $6.76 \times 10^5$ | 0 | >99.9 |
| Example 9 | $7.26 \times 10^5$ | 0 | >99.9 |
| Example 10 | $6.95 \times 10^5$ | 0 | >99.9 |
| Example 11 | $5.83 \times 10^5$ | 0 | >99.9 |
| Example 12 | $7.01 \times 10^5$ | 0 | >99.9 |
| Example 13 | $6.94 \times 10^5$ | 0 | >99.9 |
| Example 14 | $7.21 \times 10^5$ | 0 | >99.9 |
| Example 15 | $6.72 \times 10^5$ | 0 | >99.9 |

TABLE 6

Antimicrobial activity with *Escherchia coli* as test solution (based on AATCC 100 under static contact conditions)

| | Colony Density (CFU/cm$^2$) | | Antimicrobial |
|---|---|---|---|
| | 0 h | 24 h | Activity (%) |
| Control | $5.82 \times 10^5$ | $7.53 \times 10^7$ | 0 |
| Example 1 | $6.13 \times 10^5$ | 0 | >99.9 |
| Example 2 | $5.24 \times 10^5$ | 0 | >99.9 |
| Example 3 | $5.57 \times 10^5$ | 0 | >99.9 |
| Example 4 | $5.75 \times 10^5$ | 0 | >99.9 |
| Example 5 | $7.64 \times 10^5$ | 0 | >99.9 |
| Example 6 | $6.83 \times 10^5$ | 0 | >99.9 |
| Example 7 | $7.05 \times 10^5$ | 0 | >99.9 |
| Example 8 | $5.96 \times 10^5$ | 0 | >99.9 |
| Example 9 | $6.36 \times 10^5$ | 0 | >99.9 |
| Example 10 | $5.93 \times 10^5$ | 0 | >99.9 |
| Example 11 | $6.73 \times 10^5$ | 0 | >99.9 |
| Example 12 | $7.17 \times 10^5$ | 0 | >99.9 |
| Example 13 | $6.73 \times 10^5$ | 0 | >99.9 |
| Example 14 | $6.58 \times 10^5$ | 0 | >99.9 |
| Example 15 | $5.87 \times 10^5$ | 0 | >99.9 |

It can be known from tables 3, 4, 5, and 6 that, the polypeptide chlorides prepared by the preparation method of the present invention are shown to have good antimicrobial activity for the Gram-positive and Gram-negative bacteria. Moreover, by using the preparation method of the present invention, an antimicrobial polymer can be easily prepared by oxidization with hypohalites. Thus, the present invention provides a simple method of preparing an antimicrobial agent having antimicrobial efficacy.

E. Quantitative Antimicrobial Test at Minimum Antimicrobial Concentration

The evaluation in this test was carried out according to the antimicrobial standard of ASTM E2149 under dynamic contact conditions. 0.1-10 wt % of aqueous polyglutamic acid chloride solutions were prepared from the polyglutamic acid chloride in the example 5 (for details, see table 7), and the antimicrobial activities of polyglutamic acid chlorides in the aqueous polyglutamic acid chloride solutions and control were determined, respectively. It can be known from table 7 that, when the polyglutamic acid chloride is tested at 0.1 wt %, that is, 100 ppm of the N-halamine group is contained in the aqueous polyglutamic acid chloride solution, the antimicrobial activity is 95.2%; when the polyglutamic acid chloride is tested at 10 wt %, that is, 10000 ppm of the N-halamine group is contained in the aqueous polyglutamic acid chloride solution, the antimicrobial activity is greater than 99.9%.

TABLE 7

| | Colony Density (CFU) | | Antimicrobial Activity |
| --- | --- | --- | --- |
| | 0 h | 24 h | (%) |
| Control | $2.76 \times 10^5$ | $7.97 \times 10^7$ | 0 |
| 0.1 wt % | $3.61 \times 10^5$ | $7.05 \times 10^5$ | 95.2 |
| 0.2 wt % | $2.78 \times 10^5$ | 0 | >99.9 |
| 0.3 wt % | $3.84 \times 10^5$ | 0 | >99.9 |
| 0.4 wt % | $4.11 \times 10^5$ | 0 | >99.9 |
| 0.5 wt % | $3.56 \times 10^5$ | 0 | >99.9 |
| 0.6 wt % | $3.78 \times 10^5$ | 0 | >99.9 |
| 0.7 wt % | $3.91 \times 10^5$ | 0 | >99.9 |
| 0.8 wt % | $2.97 \times 10^5$ | 0 | >99.9 |
| 0.9 wt % | $2.57 \times 10^5$ | 0 | >99.9 |
| 10 wt % | $3.02 \times 10^5$ | 0 | >99.9 |

It can be known from table 7 that, when the content of the N-halamine group in the aqueous solution is 100 ppm, the bacterial growth can be suppressed. Thus, the antimicrobial agent prepared by the preparation method of the present invention has antimicrobial efficacy, only if the content of the N-halamine group in the antimicrobial agent is not less than 100 ppm.

However, the descriptions above only are preferred examples of the present invention and are not intended to limit the scope of the present invention, and simple and equivalent changes or modifications, made by any person skilled in the art without departing the spirit and scope of the present invention, all fall within the scope of the present invention.

What is claimed is:

1. A method of preparing a biodegradable antimicrobial agent, comprising:
    (a) forming an aqueous polypeptide solution by dissolving a polypeptide into an aqueous solution, wherein the polypeptide compound is polyglutamic acid or polyaspartic acid, and an added amount of the polypeptide in the aqueous polypeptide solution is 100 parts by weight;
    (b) providing an aqueous sodium hypochlorite solution, wherein an added amount of the sodium hypochlorite in the aqueous sodium hypochlorite solution is 5-130 parts by weight;
    (c) adding the aqueous sodium hypochlorite solution into the aqueous polypeptide solution to form a mixture; and
    (d) mixing the mixture for at least 1 min, such that the polypeptide compound reacts with sodium hypochlorite in the aqueous sodium hypochlorite solution, thereby forming a polypeptide chloride having at least one N-halamine group of N—Cl, wherein the polypeptide chloride is polyglutamic acid chloride or polyaspartic acid chloride.

2. The method of claim 1, wherein an added amount of sodium hypochlorite in the aqueous sodium hypochlorite solution is 35-50 parts by weight.

3. The method of claim 1, wherein the polypeptide chloride has 0.3-15 wt % of the N-halamine group.

4. The method of claim 1, wherein the antimicrobial agent contains no less than 100 ppm of the N-halamine group.

5. The method of claim 1, wherein the antimicrobial agent contains 100-10000 ppm of the N-halamine group.

6. The method of claim 1, wherein the antimicrobial agent contains 200-10000 ppm of the N-halamine group.

7. The method of claim 1, wherein the mixture has a pH of 6-8.

8. The method of claim 7, wherein the mixture further comprises a pH buffer agent.

9. The method of claim 8, wherein the pH buffer agent is an aqueous phosphoric acid solution, aqueous ammonium chloride solution, aqueous acetic acid solution, aqueous sodium hydrogen phosphate solution, aqueous disodium hydrogen phosphate solution, aqueous benzoic acid solution, or a mixture thereof.

10. The method of claim 1, wherein the mixing time of the mixture at room temperature is not less than 30 min.

11. The method of claim 1, wherein the mixing time of the mixture at room temperature is 90-180 min.

12. The method of claim 1, wherein the step (d) further comprises a step of applying an external force to the mixture to agitate it.

13. The method of claim 1, wherein the step (d) is followed by a step of: (e) adding a non-solvent to precipitate the polypeptide chloride.

14. The method of claim 13, wherein the non-solvent is isopropanol, methanol, ethanol, acetone, acetonitrile, or a mixture thereof.

15. The method of claim 1, wherein the reaction in the step (d) is performed at room temperature.

* * * * *